(12) United States Patent  (10) Patent No.: US 8,172,627 B2
Gleason et al.  (45) Date of Patent: May 8, 2012

(54) ELECTRICAL CONNECTOR WITH PLATED PLUG AND RECEPTACLE

(75) Inventors: Kenneth R. Gleason, Harrisburg, PA (US); Navin Kanjibhai Patel, Mechanicsburg, PA (US); Mark A. Hippert, Rochester, NY (US); Valentino Girolamo, Spencerport, NY (US); Laurence A. Daane, Newberg, OR (US)

(73) Assignee: Tyco Electronics Corporation, Berwyn, PA (US)

( * ) Notice: Subject to any disclaimer, the term of this patent is extended or adjusted under 35 U.S.C. 154(b) by 0 days.

(21) Appl. No.: 12/327,244

(22) Filed: Dec. 3, 2008

(65) Prior Publication Data

US 2010/0136856 A1   Jun. 3, 2010

(51) Int. Cl.
*H01R 13/02* (2006.01)
*H01R 9/24* (2006.01)

(52) U.S. Cl. ........................................ 439/886; 439/931

(58) Field of Classification Search .................. 439/886, 439/931, 86, 290
See application file for complete search history.

(56) References Cited

U.S. PATENT DOCUMENTS

| | | | |
|---|---|---|---|
| 3,363,221 A * | 1/1968 | Stark | 439/585 |
| 3,944,727 A | 3/1976 | Elliott | |
| 3,993,802 A | 11/1976 | Polichette | |
| 4,160,050 A | 7/1979 | Nuzzi | |
| 4,199,623 A | 4/1980 | Nuzzi | |
| 4,208,255 A | 6/1980 | Stahl | |
| 4,222,778 A | 9/1980 | Nuzzi | |
| 4,239,813 A | 12/1980 | Murakami | |
| 4,259,113 A | 3/1981 | Nuzzi | |
| 4,287,253 A | 9/1981 | Leech | |
| 4,293,592 A | 10/1981 | Morishita | |
| 4,301,196 A | 11/1981 | McCormack | |
| 4,339,303 A | 7/1982 | Frisch | |
| 4,391,841 A | 7/1983 | Zeblisky | |
| 4,424,095 A | 1/1984 | Frisch | |
| 4,430,154 A | 2/1984 | Stahl | |
| 4,457,952 A | 7/1984 | Kawamoto | |
| 4,511,597 A | 4/1985 | Teng | |
| 4,522,850 A | 6/1985 | Leech | |
| 4,594,311 A | 6/1986 | Frisch | |
| 4,645,732 A | 2/1987 | Young | |
| 4,668,532 A | 5/1987 | Moisan | |
| 4,748,056 A | 5/1988 | Nuzzi | |
| 4,814,197 A | 3/1989 | Duffy | |
| 4,837,129 A | 6/1989 | Frisch | |
| 4,871,319 A | 10/1989 | Babow | |
| 4,872,844 A | 10/1989 | Grebe | |
| 4,908,242 A | 3/1990 | Hughes | |

(Continued)

FOREIGN PATENT DOCUMENTS

WO   WO-2008/059248 A1   5/2008

OTHER PUBLICATIONS

International Search Report for International Application No. PCT/US2009/006358, Dated Mar. 29, 2010.

*Primary Examiner* — Javaid Nasri

(57) ABSTRACT

An electrical connector is disclosed. The electrical connector has a plug and a receptacle that are connectable in a mated position. At least one of the plug and the receptacle have a body and an electrically conductive layer applied directly to the body.

13 Claims, 15 Drawing Sheets

U.S. PATENT DOCUMENTS

| | | |
|---|---|---|
| 4,921,453 A | 5/1990 | O'Brien |
| 4,981,725 A | 1/1991 | Nuzzi |
| 4,995,824 A * | 2/1991 | Falco ............................ 439/290 |
| 5,012,807 A | 5/1991 | Stutz, Jr. |
| 5,047,114 A | 9/1991 | Frisch |
| 5,109,479 A | 4/1992 | Williams |
| D341,817 S | 11/1993 | Huang |
| 5,258,200 A | 11/1993 | Mayernik |
| 5,338,567 A | 8/1994 | Kohm |
| 5,407,622 A | 4/1995 | Cleveland |
| 5,429,861 A | 7/1995 | Mayernik |
| 5,626,483 A | 5/1997 | Naitoh |
| 6,473,045 B1 | 10/2002 | Duquerroy |
| 2003/0073348 A1 | 4/2003 | Ries et al. |

* cited by examiner

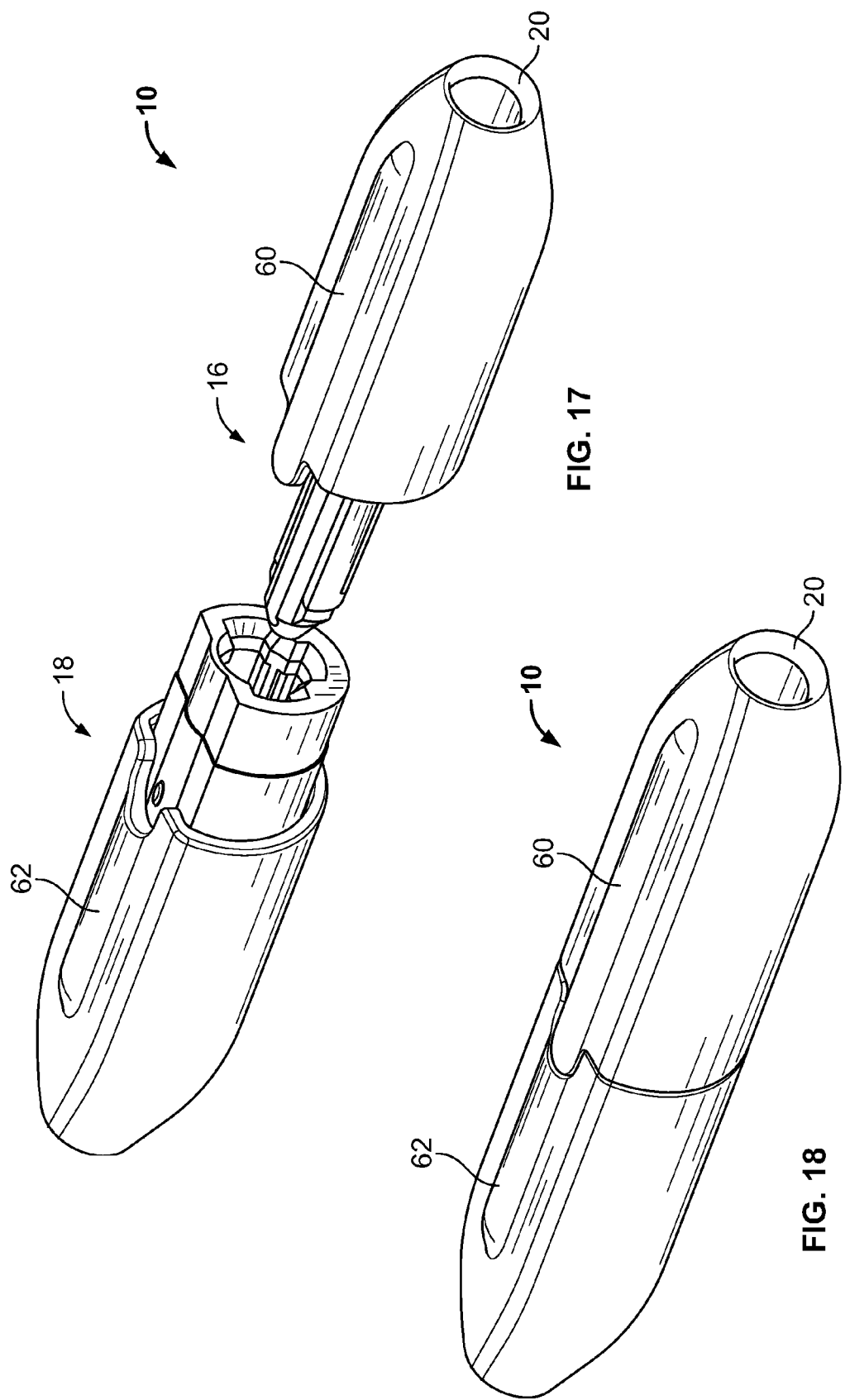

ELECTRICAL CONNECTOR WITH PLATED PLUG AND RECEPTACLE

FIELD OF THE INVENTION

The present invention is directed to electrical connectors and electrical connector assemblies, and more particularly, to electrical connectors and electrical connector assemblies with plated conductors that provide electrical connections between a plug and receptacle.

BACKGROUND OF THE INVENTION

Circular electrical connectors typically include a housing in which a plurality of discrete male and/or female electrical contacts are held. The electrical contacts are arranged within the housing in a pattern about a common central longitudinal axis of the housing. However, the pattern about the common central longitudinal axis may make it difficult to reduce the overall size of the circular electrical connector or manufacture connectors, especially where disposable connectors are needed.

Therefore, there is a need for a compact electrical connector having the required electrical contacts. There is a further need for an electrical connector of compact size that is manufactured at a lower cost than previous connectors.

SUMMARY OF THE INVENTION

The present invention is directed to an electrical connector. The electrical connector has a plug and a receptacle. The receptacle is mateable with the plug. At least one of the plug or the receptacle has a plastic body with an electrically conductive layer plated directly upon the plastic body.

The present invention is also directed to a method for manufacturing an electrical connector. The method includes the steps of forming a plastic body for at least one of a plug or a receptacle and forming an interconnect pattern directly onto the plastic body. The method also includes the steps of plating an electrically conductive layer directly to the interconnect pattern.

The present invention is further directed to an electrical connector having a plug and a receptacle, the receptacle being mateable with the plug. At least one of the plug and the receptacle has a plastic body with an electrically conductive layer plated directly upon the plastic body. A cover substantially surrounds at least one of the plug and the receptacle and provides electrical insulation to at least one of the plug and the receptacle.

BRIEF DESCRIPTION OF THE DRAWINGS

FIG. 17 shows the electrical connector of FIG. 16 in an unmated position.

FIG. 18 shows the electrical connector of FIG. 16 in a mated position.

DETAILED DESCRIPTION OF THE INVENTION

Figure 1:
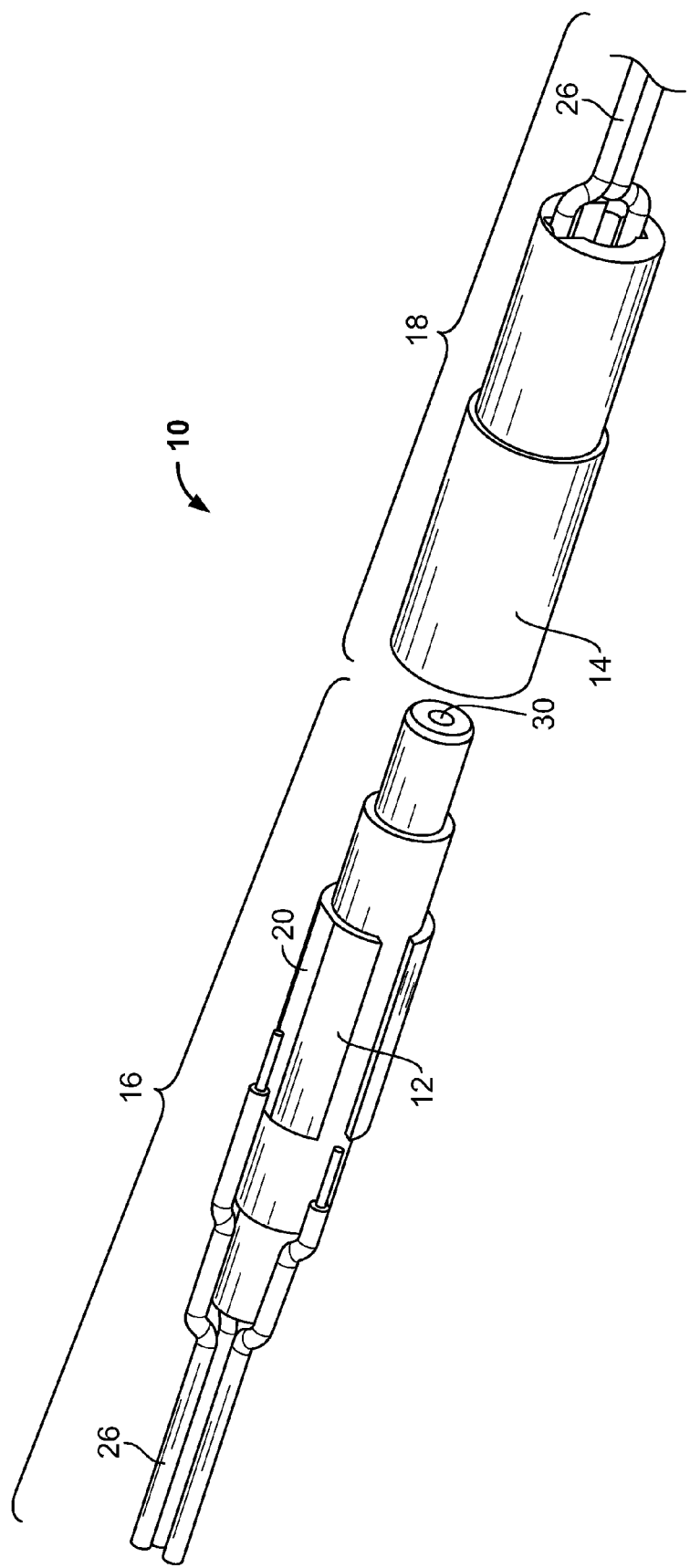
FIG. 1 shows an embodiment of an electrical connector with a plug and a receptacle in an unmated position.

The present invention will now be described more fully hereinafter with reference to the accompanying drawings in which preferred embodiments of the invention are shown. This invention may, however, be embodied in many different forms and should not be construed as limited to the embodiments set forth herein; rather, these embodiments are provided so that this disclosure will be thorough and complete and will fully convey the scope of the invention to those skilled in the art.

Molded Interconnect Devices (MID) are injection molded plastic elements incorporating electrical conductors in specific areas to carry signals, or power, or to provide shielding. The electrical conductors may be disposed in unconventional areas, thereby providing components with the capability of being mounted in various spatial directions. Further, the electrical conductors are plated on the plastic elements, which may reduce or even eliminate the need for space-consuming discrete parts that may require additional assembly processes. In addition to these space and time saving features, the injection molding process enables the creation of additional features such as recesses, channels, and openings to fulfill mechanical or electromechanical requirements of a specific application.

MID technology may incorporate any suitable plastic material such as, but not limited to, syndiotactic polystyrene (SPS) and liquid crystal polymer (LCP). In addition, any suitable process may be used for plating the electrical contact to the plastic in the MID technology including, but not limited to, laser direct structuring (LDS), laser subtractive structuring (LSS), and two shot molding. In the LDS process, the structure is molded in a standard mold using one of several proprietary plastics available, then the desired interconnect pattern is directly written on the resulting molded part and the conductive paths are plated using industry-standard methods. The plating adheres only where the plastic has been activated by the laser. These activated areas are subsequently metal plated in chemical solutions. The LSS process involves the entire surface of the connector being chemically activated and metallized. The process is carried out by means of laser ablation and/or exposure, with subsequent separation of the tracks in an etching process. The two shot molding process includes a two-stage injection molding process where two different plastic components are injected into two different molds to form a trace pattern on the surface. An electrically conductive material is plated onto the trace pattern by submersion of the plastic material into a plating bath.

In some applications, such as medical device applications where one side of the electrical connector is disposable and the other side reusable, it may be desirable to use a plated plug or receptacle in combination with a plug or receptacle using more traditional electrical interconnect components, such as, but not restricted to, metal contacts, spring pins, or conductive interposer materials.

It should be understood that while the embodiments described in this application show both plug and receptacle being intermediate between conductive cables, other embodiments might include different conductive arrangements, such as but not limited to a plug and receptacle connector of which at least the plug or receptacle uses plated contacts designed to connect two printed circuits; a cable connection to a printed circuit; or a terminal plug or receptacle containing an active or passive component.

Figure 2:
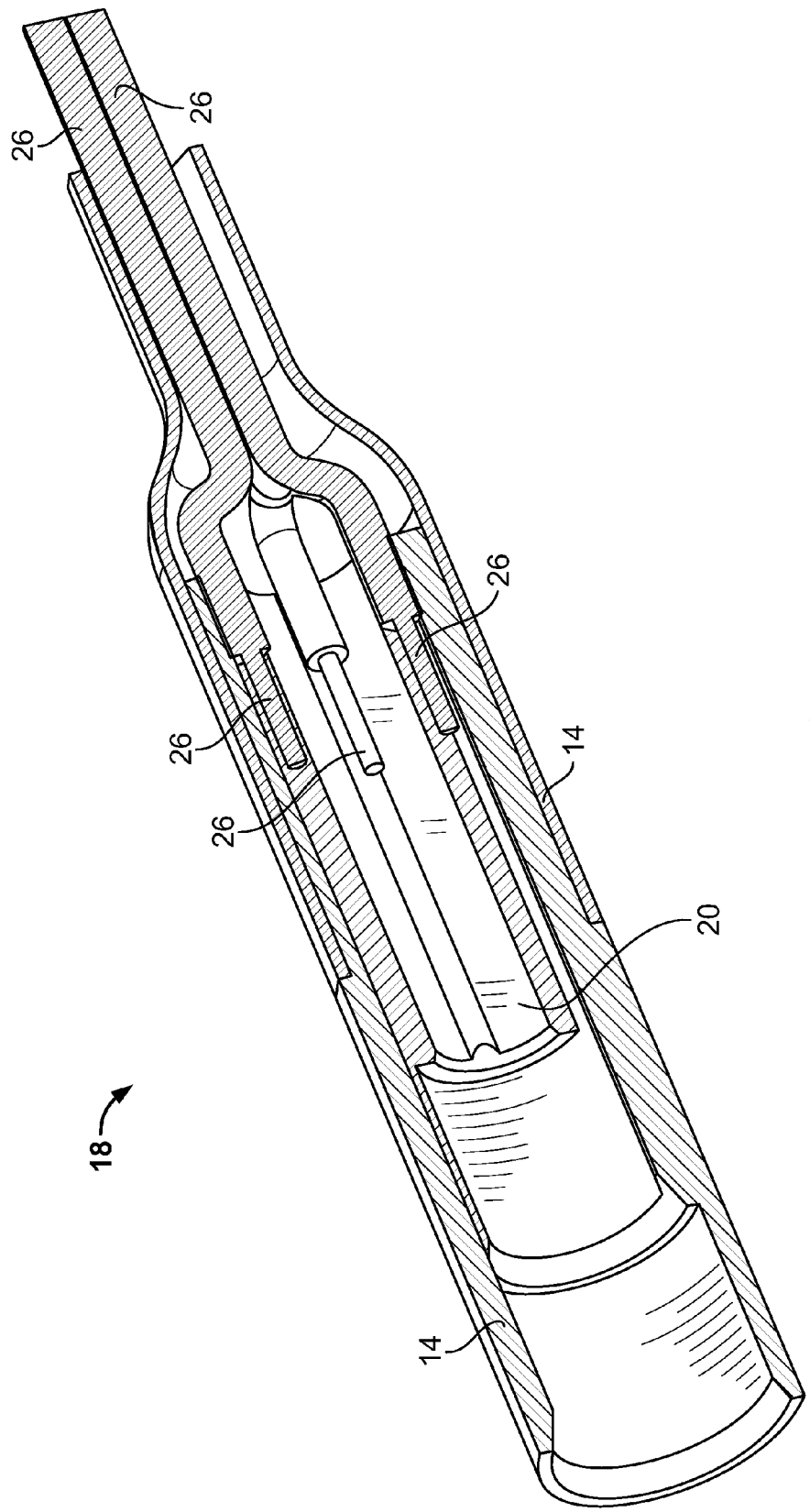
FIG. 2 shows a sectional view of the receptacle of the electrical connector of FIG. 1.
Figure 3:
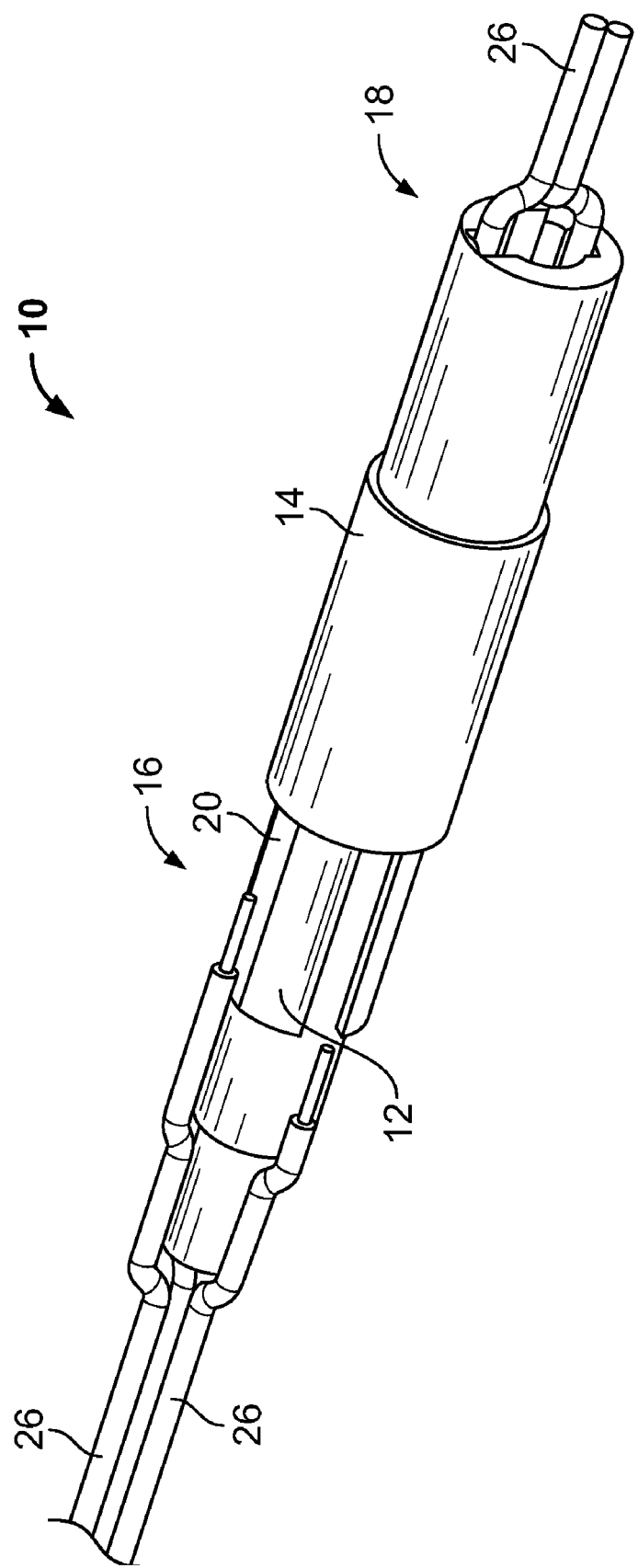
FIG. 3 shows the electrical connector of FIG. 1 with the plug and receptacle in a mated position.

Referring now to FIGS. 1-3, an embodiment for an electrical connector 10 is shown. Electrical connector 10 includes a plug 16 mateable with a receptacle 18. Plug 16 includes a body portion 12 and an electrically conductive layer 20. Receptacle 18 includes a body portion 14 and electrically conductive layer 20. Alternately, body 12 and body 14 may be manufactured from a plastic material using an MID technology process as described in detail above. Body 12 and body 14 may also be manufactured from an injection molding process or any other suitable manufacturing process. The plastic material used in manufacture may be any plastic suitable for an MID technology process, and/or the material may be any suitable insulative material for MID technology other than plastic. At least one conductive cable 26 is terminated to electrically conductive layer 20 of plug 16 and at least one conductive cable 26 is terminated to electrically conductive layer 20 of receptacle 18. A plurality of conductive cables 26 is terminated to electrically conductive layers 20 of plug 16 and receptacle 18. Conductive cables 26 may have varying diameters or conductive cables 26 may have equal diameters. For example, if each conductive cable 26 is paired with a separate conductive layer 20, conductive layers 20 may be substantially parallel to an axis of connector 10 along the common diameter and also be electrically isolated by unplated body material. An aperture 30 may extend through body 12 and body 14, such that when mated, aperture 30 forms a continuous opening through connector 10. Additional conductors such as electrical, optical, fluidic or other suitable conductors, or tools may be disposed in aperture 30 and secured by connector 10.

Conductive layers 20 of plug 16 and conductive layers 20 of receptacle 18 are disposed in plug 16 and receptacle 18 such that one or more electrical connections are made when plug 16 and receptacle 18 are in a mated position. Physical features (not shown) such as raised bumps, ridges, textured portions or other suitable features may be applied to the surface to provide sufficient contact pressure to make a secure electrical connection between plug 16 and receptacle 18. A single conductive cable 26 may be in electrical communication with a single conductive layer 20 or with multiple conductive layers 20. Body 12 and body 14 provide electrical isolation between conductive layers 20, if required.

Figure 4:
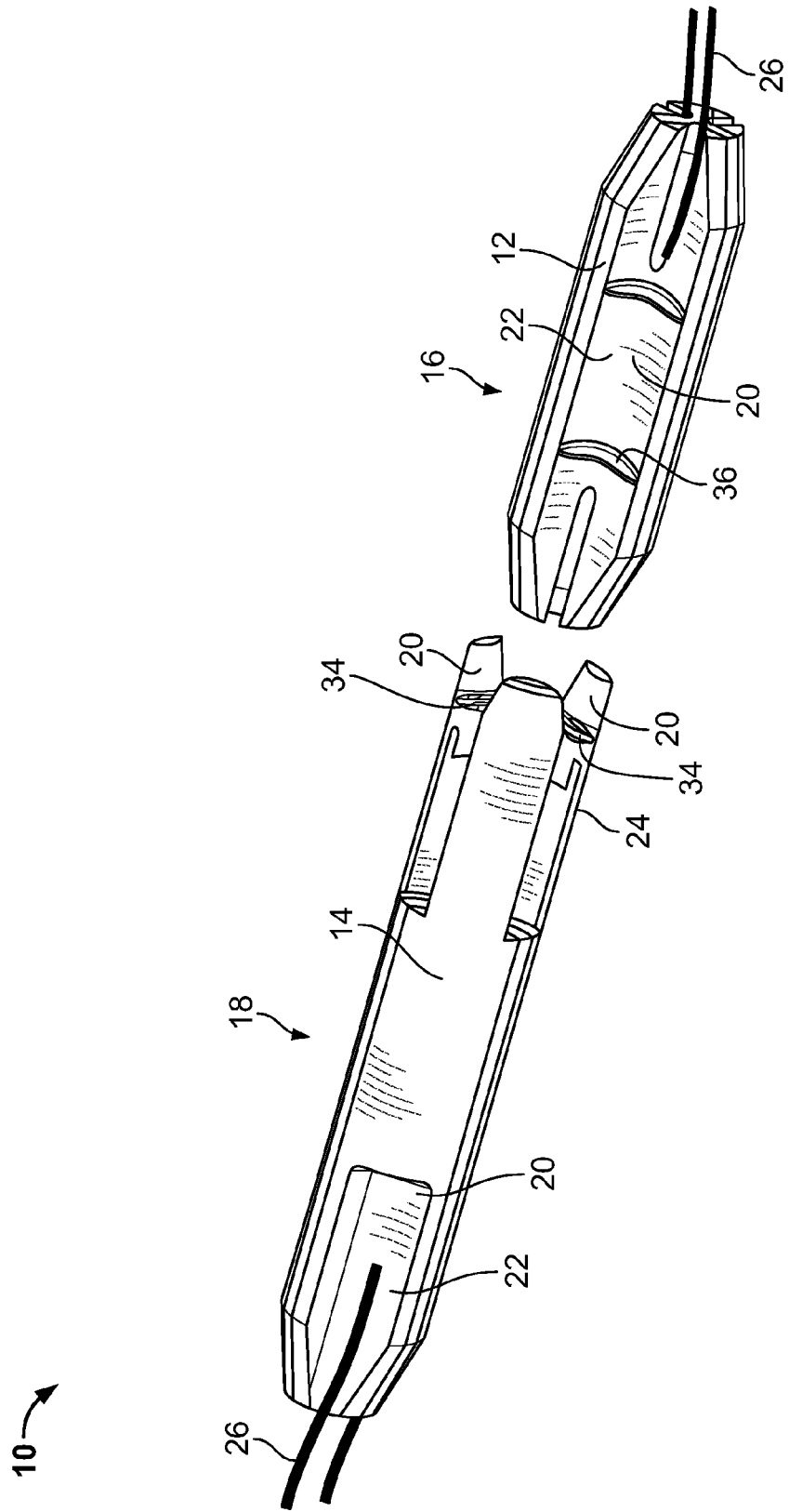
FIG. 4 shows another embodiment of an electrical connector with a plug and a receptacle in unmated position.
Figure 5:
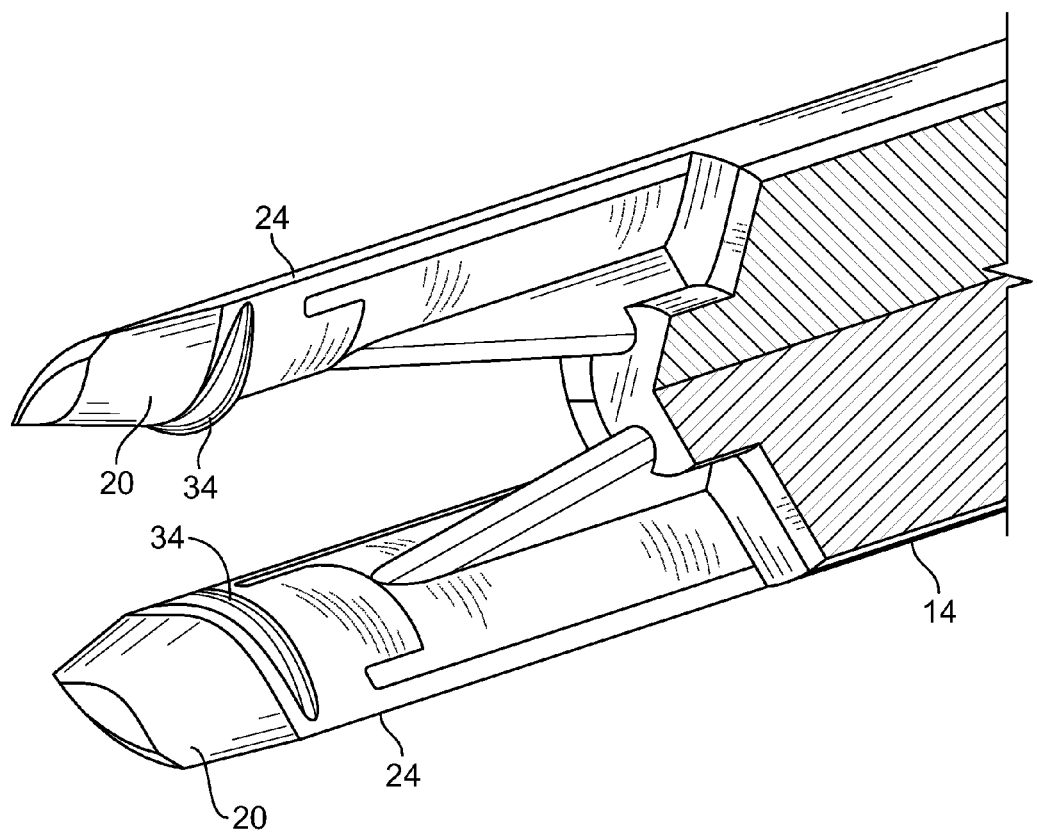
FIG. 5 shows a partially sectional view of the receptacle of FIG. 4.
Figure 6:
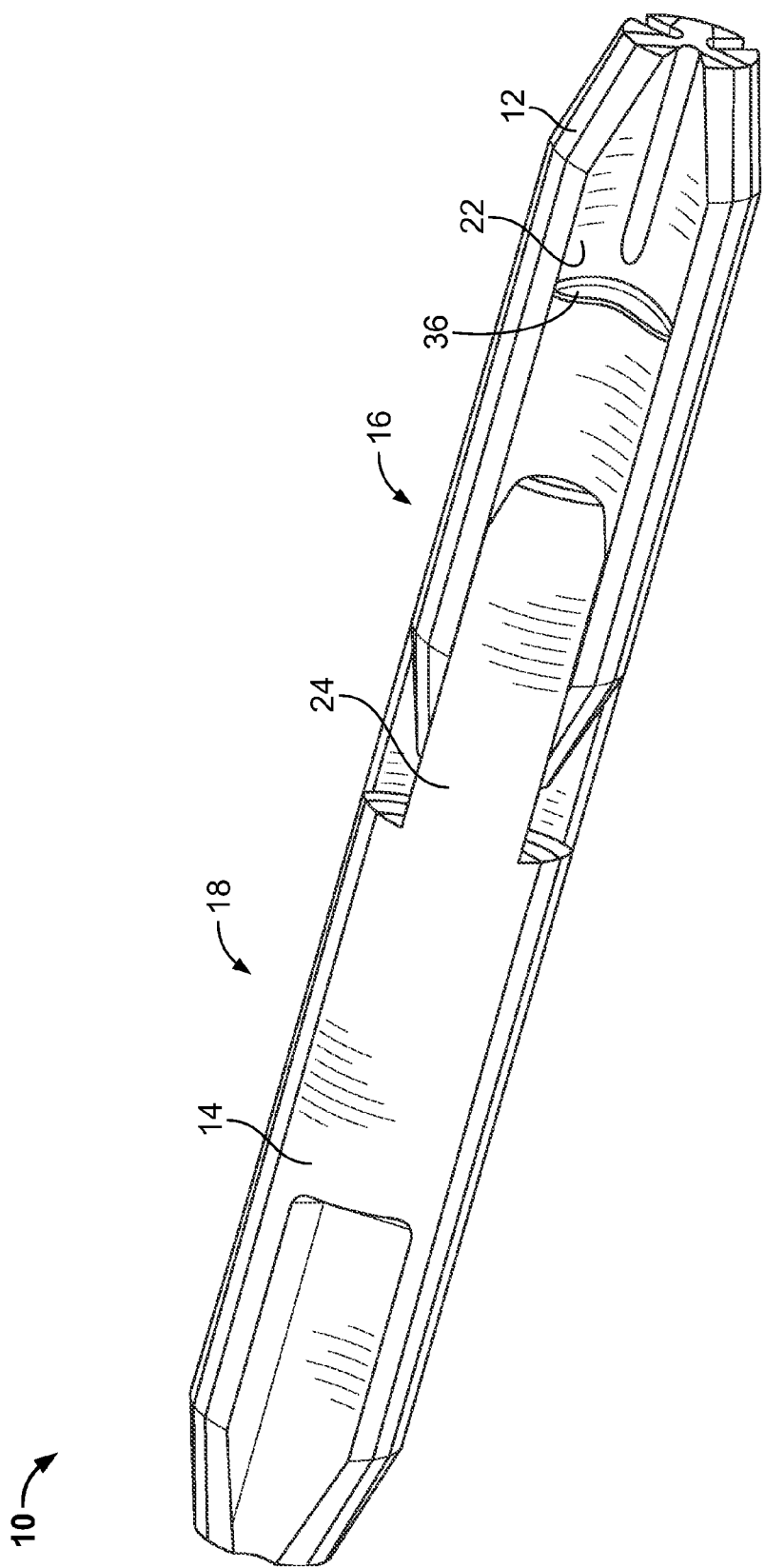
FIG. 6 shows the electrical connector of FIG. 4 with the plug and receptacle in a partially mated position.

Referring now to FIGS. 4-6 another embodiment for electrical connector 10 is shown. Electrical connector 10 includes a plug 16 mateable with a receptacle 18. Plug 16 includes body 12 and an electrically conductive layer 20. Body 12 may be manufactured from a plastic material using an MID technology process as described in detail above. Body 12 may also be manufactured from an injection molding process or any other suitable molding process. The plastic material may be any suitable plastic for the MID technology process, and/or the material may be any non-plastic insulative material suitable for MID technology. Body 12 may have a recess 22, or a plurality of recesses, that are plateable with electrically conductive layer 20. Body 12 has dimensions suitable to prevent or control electrical communication between electrically conductive layers 20 on each recess 22.

Receptacle 18 includes body 14 and electrically conductive layer 20. Body 14 may be manufactured from a plastic material with an MID technology process or from an injection molding process or any other suitable process. The plastic material may be any suitable plastic for the MID technology process, and the material may be any suitable insulative material other than plastic. Body 14 has dimensions suitable to prevent or control electrical communication between electrically conductive layers 20. Conductive cables 26 are in electrical communication with electrically conductive layer 20 and extend from an end of recess 22 and are in electrical communication with conductive cable 26.

Extending from one end of receptacle 18 is an extension 24 or a plurality of extensions 24. Extensions 24 may be plated with electrically conductive material in electrically conductive layer 20 to electrically communicate with plug 16 and conductive cable 26. Extensions 24 are in electrical communication with electrically conductive layer 20 on plug 16 when plug 16 and receptacle 18 are in a mated position. Extensions 24 may be of unitary construction with body 14, or extensions 24 may be otherwise attached and secured to body 14. Extension 24 may include tabs 34, which are configured to fit into pockets 36 in plug 16 when plug 16 is mated with receptacle 18. Tabs 34 secure plug 16 to receptacle 18 when plug 16 and receptacle 18 are in a mated position. An audible or tactile signal may be produced when tabs 34 are secured in pockets 36, notifying a user that plug 16 is mated and secure with receptacle 18. Plug 16 may have a compact size, being 13.5 mm in length and 2.5 mm in diameter, however any desired length and diameter may be used for plug 16.

Figure 7:
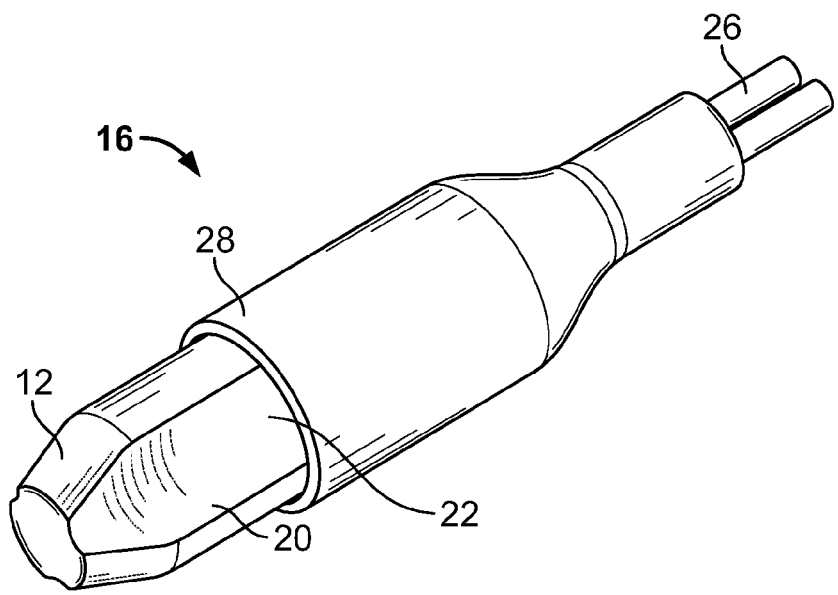
FIG. 7 shows the plug of the electrical connector of FIG. 4 with a cover.
Figure 8:
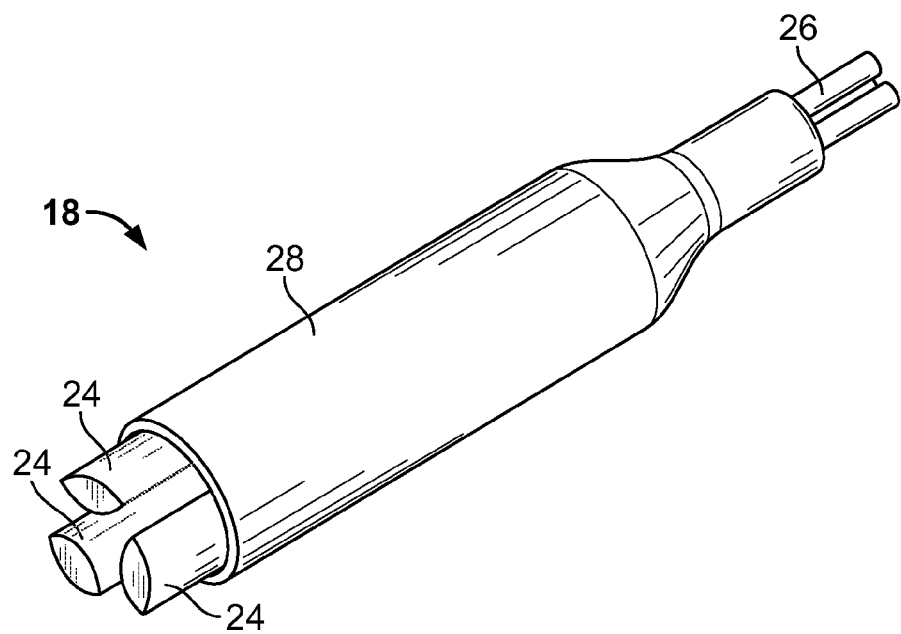
FIG. 8 shows the receptacle of the electrical connector of FIG. 4 with a cover.
Figure 9:
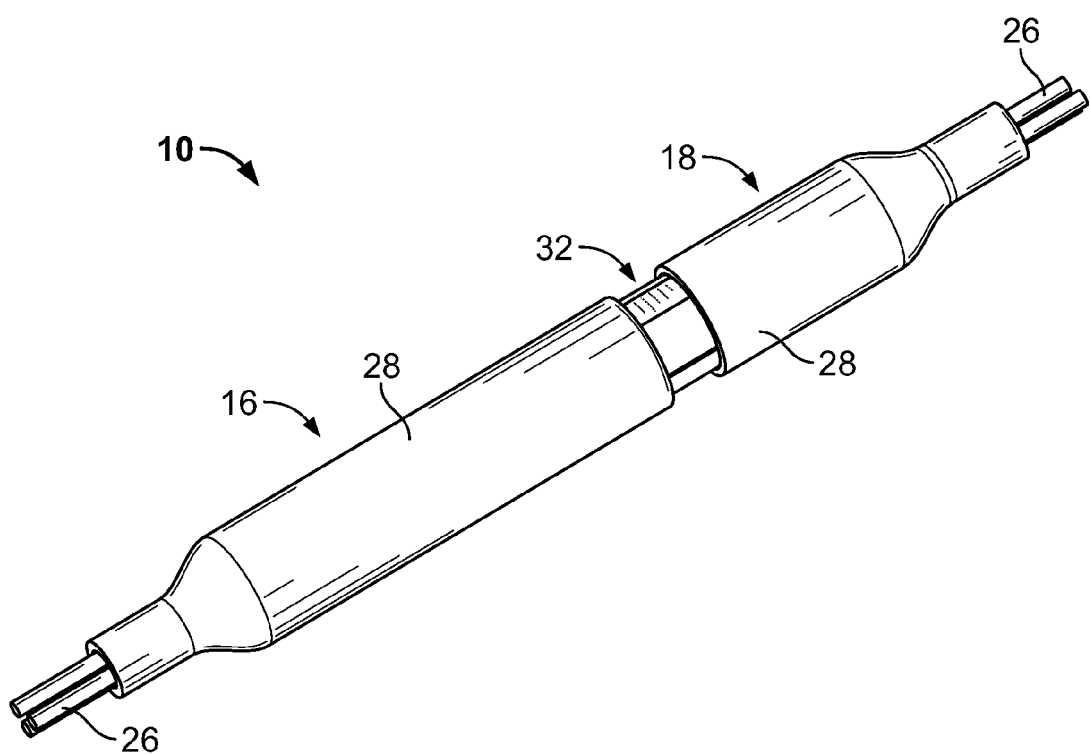
FIG. 9 shows the plug and receptacle of FIGS. 7 and 8 in a mated position.

Referring specifically to FIGS. 7-9, an insulated cover 28 substantially surrounds both plug 16 and receptacle 18. Cover 28 protects plug 16 and receptacle 18 from any object or device contacting electrically conductive layer 20, and also prevents any moisture, liquid, particles, or other harmful product from contacting electrically conductive layer 20. Cover 28 may also provide strain resistance to conductive cables 26 extending from plug 16 and receptacle 18. When plug 16 and receptacle 18 are mated, there may be a gap 32 between cover 28 on plug 16 and cover 28 on receptacle 18 when plug 16 is in a mated position with receptacle 18. When plug 16 and receptacle 18 are in a mated position, plug 16 and receptacle 18 substantially form a cylindrical configuration. Further, electrically conductive layer 20 is substantially covered and protected when plug 16 and receptacle 18 are in a mated position. When plug 16 is in a mated position with receptacle 18, plug 16 is disposed inside extensions 24, with extensions 24 filling in recess 22.

Figure 10:
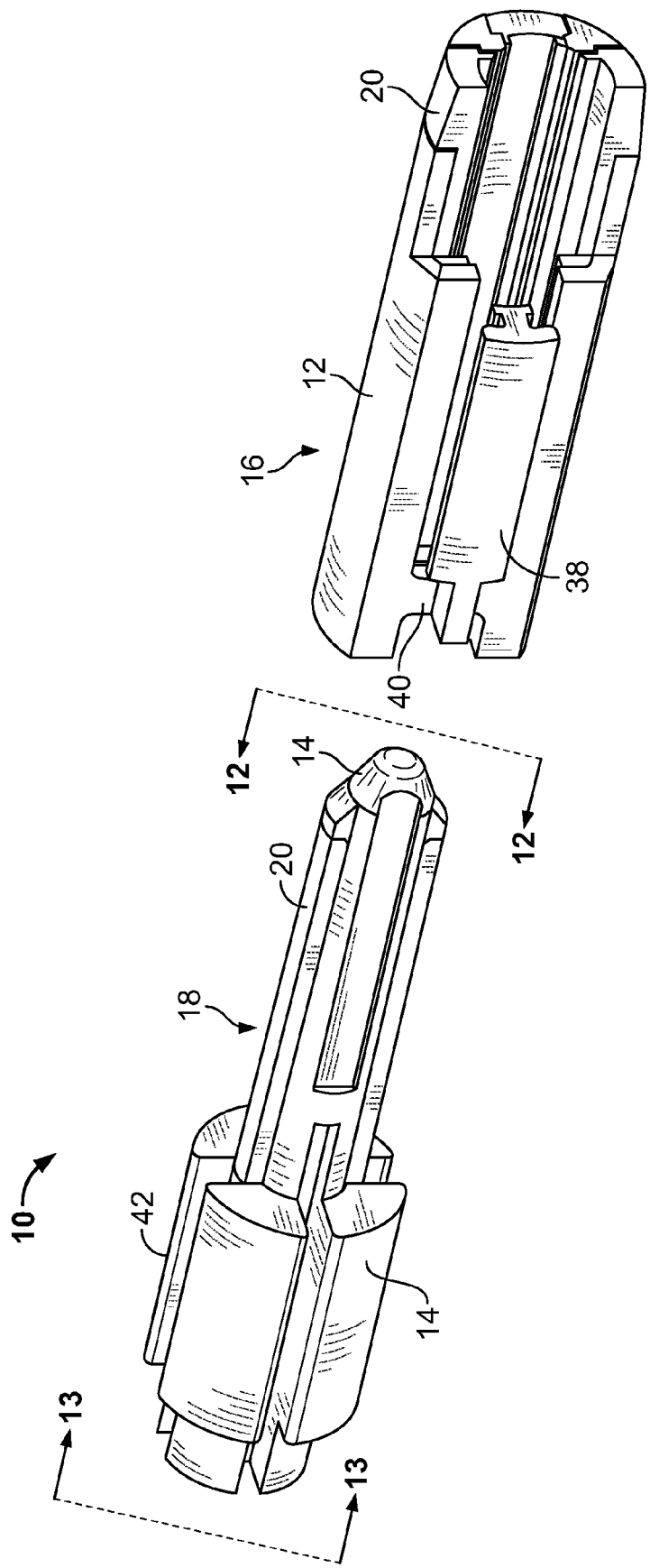
FIG. 10 shows another embodiment of an electrical connector having a plug and a receptacle and a latch, in an unmated position.
Figure 11:
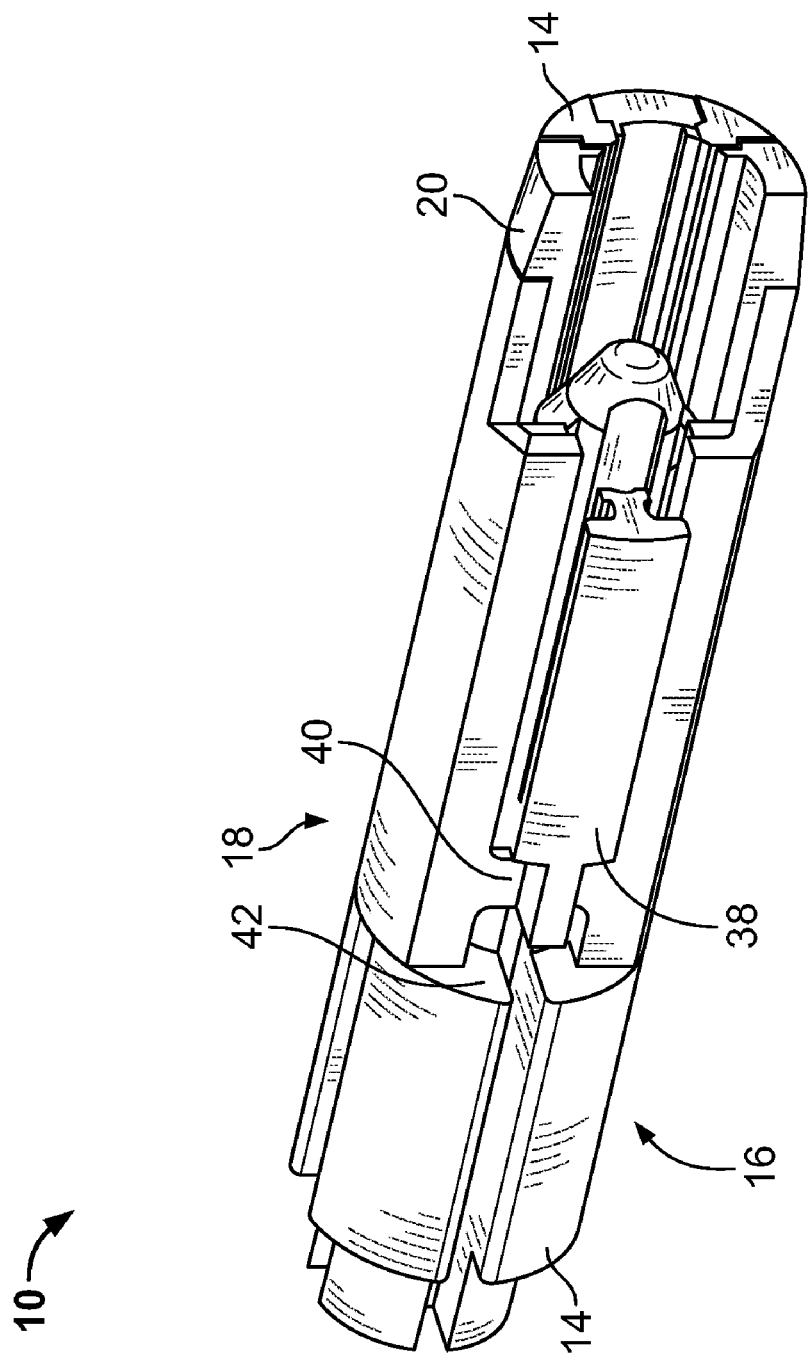
FIG. 11 shows the plug of the electrical connector of FIG. 10.

Referring now to FIGS. 10 and 11, another embodiment of connector 10 includes a plug 16 and receptacle 18. When mated, body 12 and body 14 provide insulative protection to electrically conductive layer 20. A cover (not shown) may also substantially surround connector 10 to provide additional insulative and protective covering. When plug 16 and receptacle 18 are in a mated position, latch 38 engages with a ledge 40 to secure plug 16 with receptacle 18. Latch 38 may be self-actuating or manually actuated. A tool may be required to release latch 38 and remove plug 16 from receptacle 18. A conductive cable 26 (see, e.g., FIG. 4) may be in electrical communication with plug 16 and receptacle 18 to provide electrical communication with external devices or instruments. Base 42 prevents plug 16 from being inserted too deep into receptacle 18 and aligns ledge 40 with latch 38 to secure plug 16 and receptacle 18.

Figure 12:
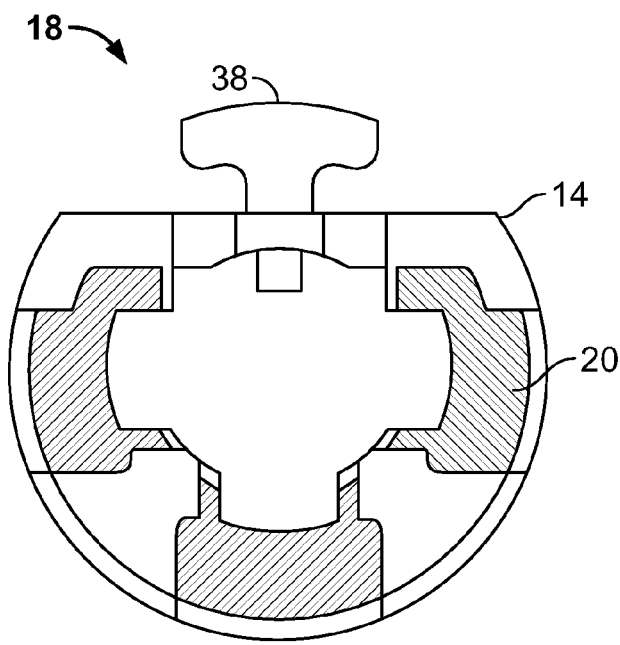
FIG. 12 shows an end view of the receptacle of FIG. 10 with end plating.
Figure 13:
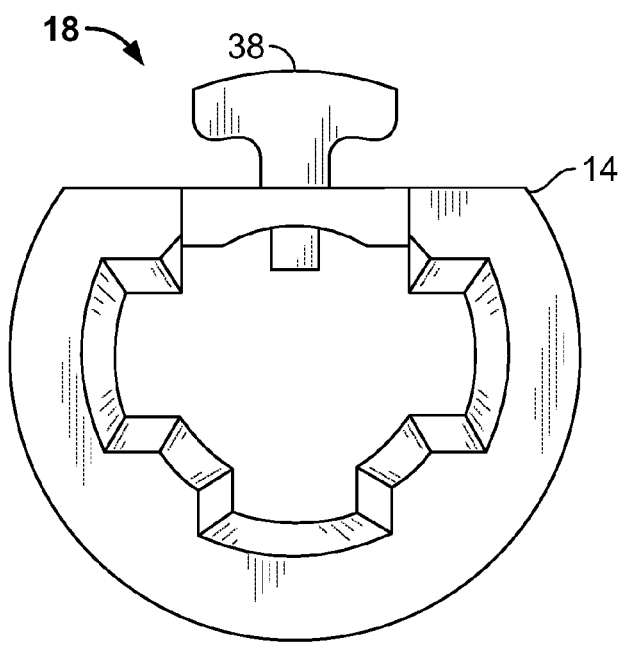
FIG. 13 shows an end view of the receptacle of FIG. 10 without end plating.

Referring now to FIGS. 12 and 13, end views of receptacle 18 are shown. Electrically conductive layer 20 is exposed on one end of receptacle 18, as shown in FIG. 12, and unexposed on the opposite end of receptacle 18, as shown in FIG. 13. Receptacle 18 is shown as having a circular, cylindrical, or other similar shape, however, any suitable shape that is capable of mating with plug 16 may be used. Latch 38 protrudes from body 14, but maintains the configuration of receptacle 18 that is capable of mating with plug 16.

Figure 14:
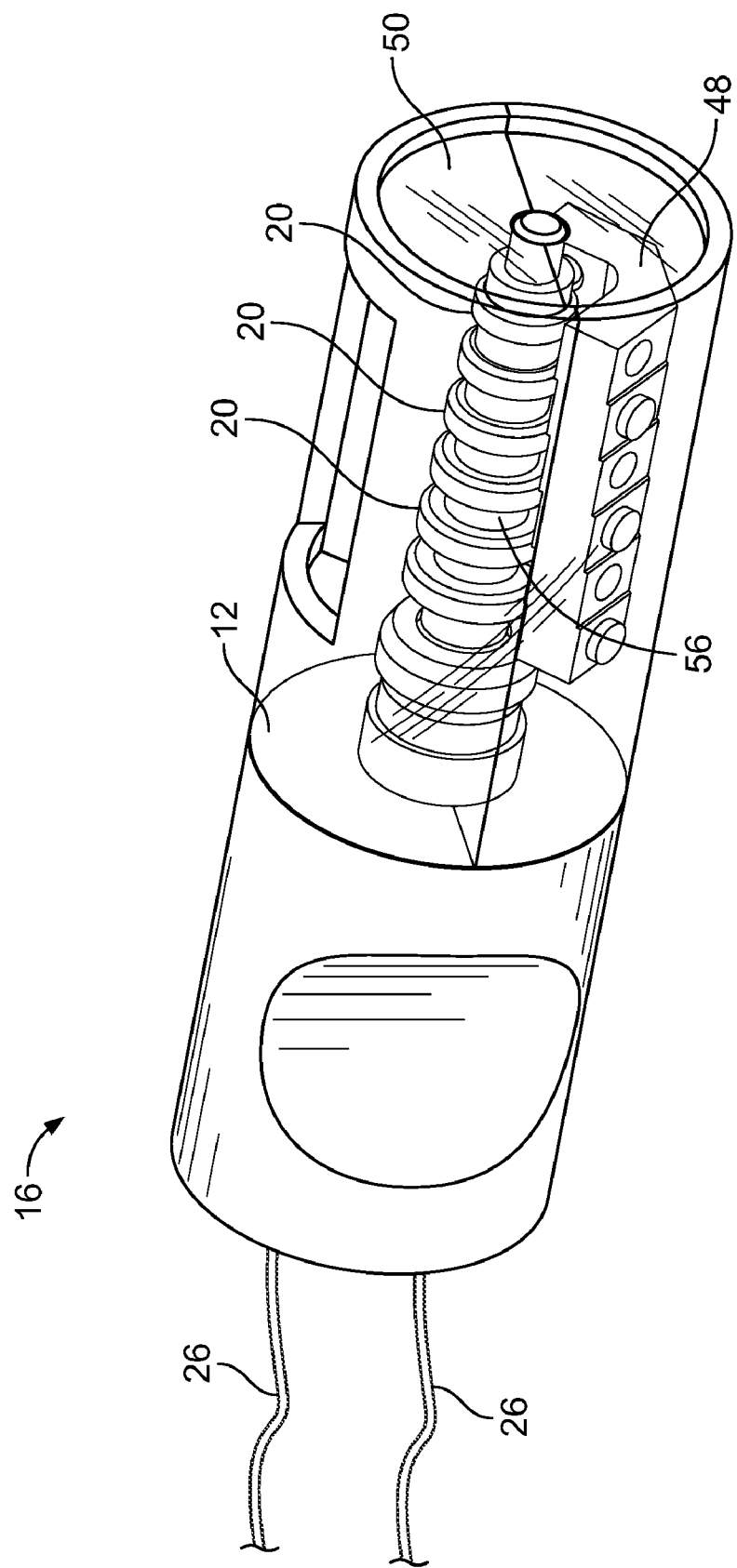
FIG. 14 shows another embodiment of an electrical connector with plug and receptacle in a mated position.
Figure 15:
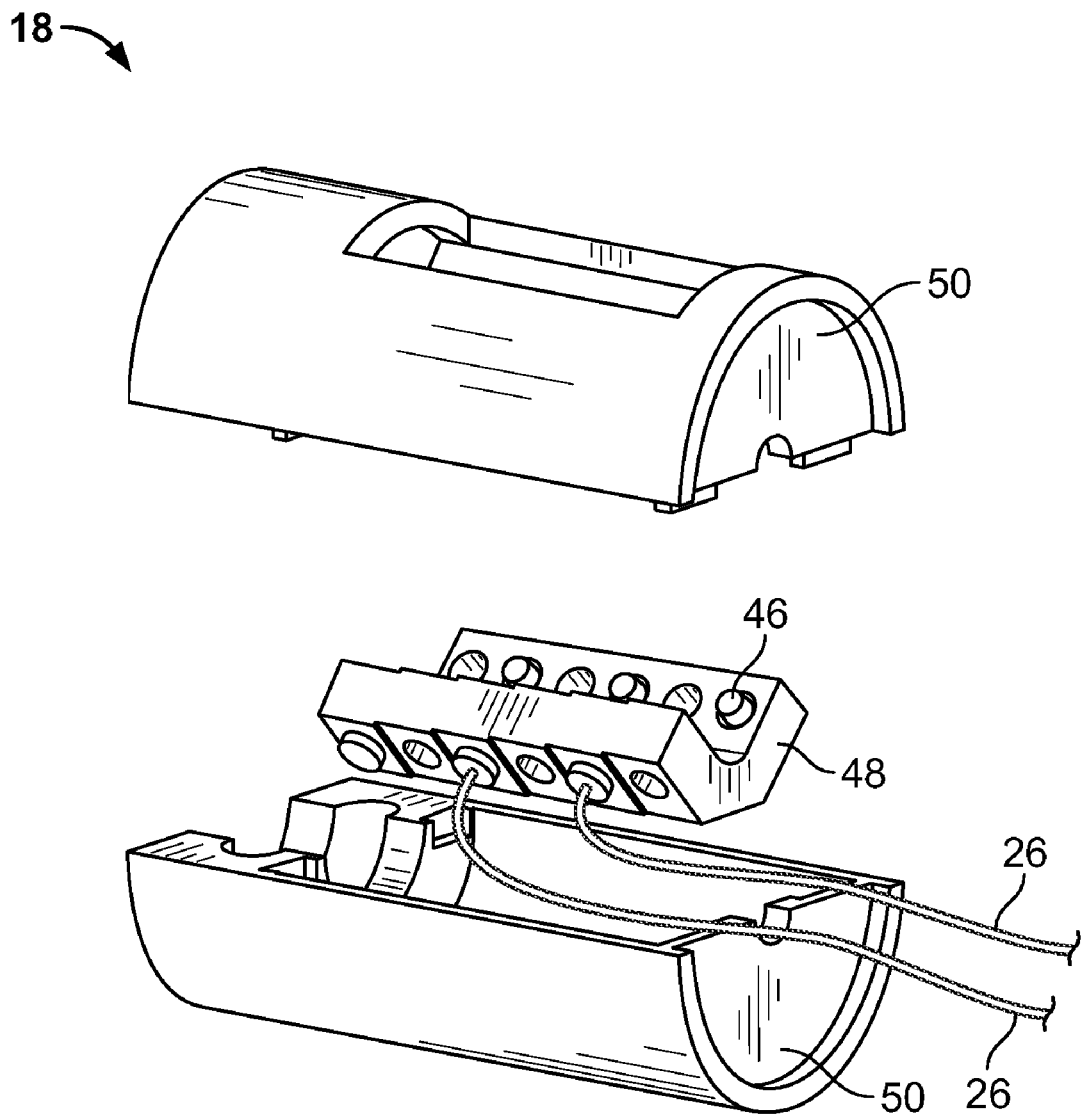
FIG. 15 shows the receptacle of the electrical connector of FIG. 14.

Referring now to FIGS. 14-15, another embodiment of connector 10 is shown having plug 16 and receptacle 18. Plug 16 is plated, i.e. body 12 is manufactured from a MID process with a plastic or other suitable material for an MID process. An electrically conductive layer. Body 12 is configured with a conical shape having threads 56 similar to that of a screw or other suitable device. The outmost surface of threads 56 are plated with electrically conductive layer 20 for contacting electrically conductive contact portions 46 in receptacle 18. Plug 16 may be rotatably threaded in receptacle 18. Plug 16 may also be inserted and secured into receptacle 18 by a linear insertion force.

The interconnection between plug 16 and receptacle 18 provides movement during connectivity while maintaining an electrical connection between plug 16 and receptacle 18. For example, plug 16 may be rotated while inserted in receptacle 18 while maintaining an electrical connection between plug 16 and receptacle 18. Conductive cables 26 are disposed in a central passageway 58 in plug 16. Apertures 44 are disposed and arranged to provide an opening through which conductive cables 26 may protrude and be secured to electrically conductive layer 20. A solder connection or other suitable connection such as a weld may be used to secure conductive cable 26 to electrically conductive layer 20.

Receptacle 18 includes a housing 50 and a header 48. Housing 50 is shown as having two pieces, however, housing 50 may be a single piece, or may contain more than two pieces. Housing 50 provides mechanical protection and electrical insulation to header 48 and other internal components disposed within housing 50. Header 48 contains electrical contact points 46, such as spring pins or any other suitable device for contacting electrically conductive layer 20 in plug 16. Conductive cables 26 are in electrical communication with electrical contact points 46. FIG. 14 shows a direct connection between conductive cable 26 and electrical contact points 46, however a PCB interface may be used to electrically connect electrical contact points 46 and conductive cable 26. While FIG. 14 shows plug 16 having body 14 and electrically conductive layer 20 and receptacle 18 having header 48 and electrical contact points 46 for electrically communicating with plug 16, it is understood that plug 16 may include header 48 and electrical contact points 46 and receptacle 18 may include electrically conductive layer 20. It is also understood that both plug 16 and receptacle 18 may have plated electrically conductive layer 20.

Figure 16:
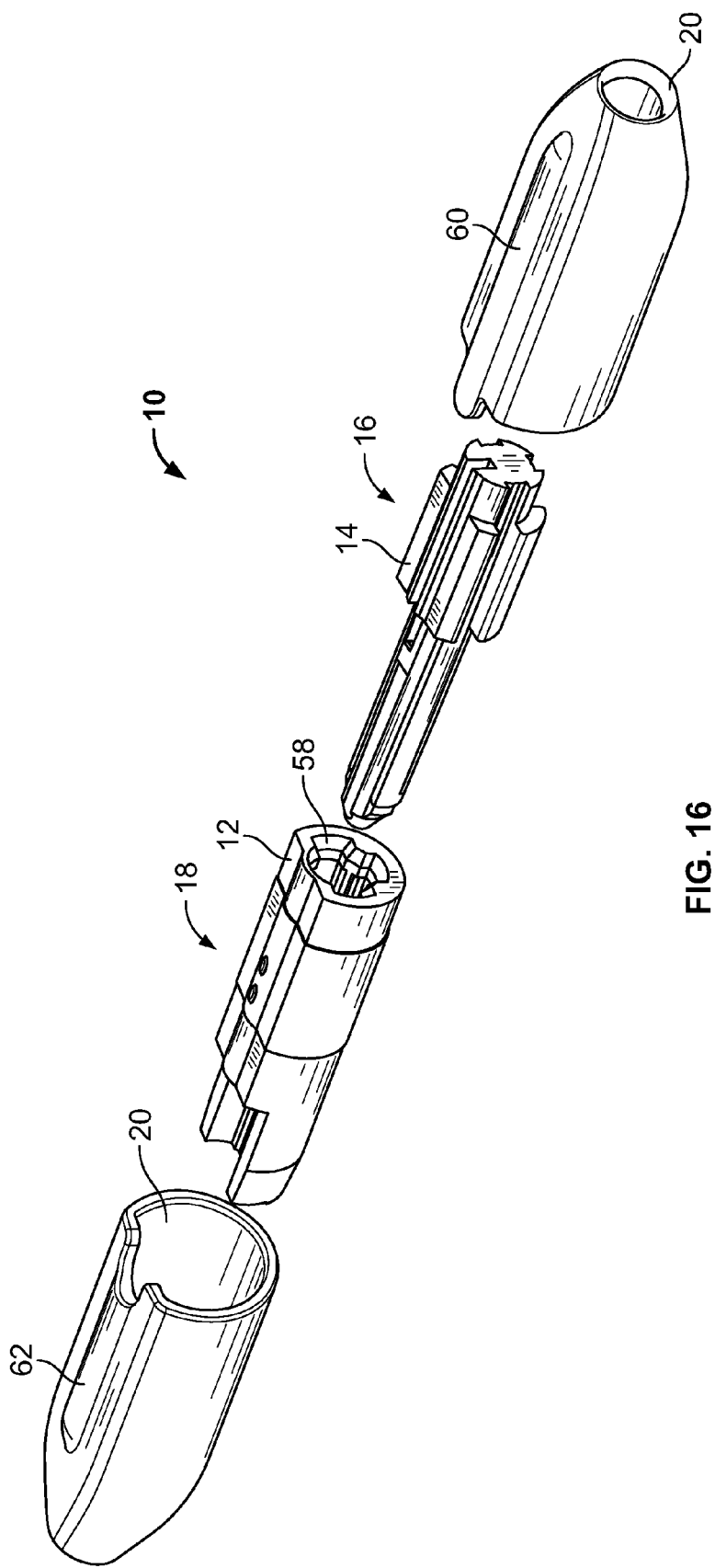
FIG. 16 shows a partially exploded view of an electrical connector.

Referring now to FIGS. 16-18, another embodiment for connector 10 is shown. Connector 10 includes a plug 16 and receptacle 18 that are mateable to create an electrical connection. Plug 16 includes a plug shell 60 and body 12. Plug shell 60 provides mechanical protection and electrical isolation to body 12. Receptacle 18 includes a receptacle shell 62 and body 14. Receptacle shell 62 provides mechanical protection and electrical isolation to body 142. While plug shell 60 and receptacle shell 62 have been shown as single integrated parts, plug shell 60 and receptacle shell 62 may also be made from a plurality of parts. For example, plug shell 60 and/or receptacle shell 62 may be a two-piece arrangement that is closed and secured around body 12 or body 14.

Plug shell 60 and receptacle shell 62 include plated electrically conductive layer 20 to provide electromagnetic communication to plug 16 and receptacle 18, respectively. Conductive cables 26 may be secured to plug 16 and/or receptacle 18. Conductive cables 26 may protrude from one end of plug 16 or receptacle 18 and be secured to electrically conductive layer 20 to provide electrical communication to plug 16 and receptacle 18. Body 14 includes plated electrically conductive layer 20 on the exterior surface to contact electrically conductive layer 20 on the interior of receptacle shell 62 and electrically conductive layer 20 on the interior of plug shell 60.

Plug shell 60 and receptacle shell 62 may be secured to body 12 and body 14 by the use of adhesives, mechanical features such as, but not limited to, an interference fit, detents, or latch, ultrasonic welding, soldering, or any other suitable securing means. Plug shell 60 and receptacle shell 62 are secured to body 12 and body 14 such that substantially all movement between plug shell 60 and body 12 and receptacle shell 62 and body 14 is prevented and such that plug shell 60 and receptacle shell 62 are not easily removable from body 12 and body 14. When plug 16 and receptacle 18 are in the mated position, plug shell 60 and receptacle shell 62 substantially surround body 12 and body 14.

Any suitable application for all of the above-described connectors may be used, including, but not limited to medical applications such as a catheter. In addition, an MID process may be used to manufacture the above-described connectors. During the MID process, it is understood that the body may be created before the electrically conductive layer is plated to the body material, or the body may be formed after the electrically conductive layer is manufactured.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An electrical connector for making multiple electrical connections, said connector comprising:
   a plug comprising a plastic body comprising an electrically conductive layer plated directly on at least a portion of the plastic body of the plug; and
   a receptacle comprising a plastic body comprising an electrically conductive layer plated directly on at least a portion of the plastic body of the receptacle, the receptacle being mateable with the plug such that when a plurality of conductive cables are positioned adjacent the plug, said cables are terminated to the electrical conductive layer of the plug and the electrically conductive layer of the receptacle.

2. The electrical connector of claim 1, wherein the plug and the receptacle comprise a substantially cylindrical shape.

3. The electrical connector of claim 1, wherein the electrically conductive layer is plated on the body with a molded interconnect device technology.

4. The electrical connector of claim 1, wherein the plug comprises a fastening device to secure the receptacle in the plug.

5. The electrical connector of claim 1, wherein the electrically conductive layer is plated directly to an inside surface of the body of the plug or the receptacle.

6. The electrical connector of claim 1, wherein the electrically conductive layer is plated directly to an outside surface of the body of the plug or the receptacle.

7. The electrical connector of claim 1, wherein the body of the plug or the receptacle comprises at least one recess, electrically isolated from an adjacent recess, the at least one recess being plated with the electrically conductive layer.

8. The electrical connector of claim 1, wherein at least one of the plug and the receptacle comprises a cover.

9. The electrical connector of claim 1, wherein at least one of the plug and the receptacle are rotatable when the plug and the receptacle are in a mated position.

10. The electrical connector of claim 1, further comprising a cover, the cover substantially surrounding at least one of the plug and the receptacle, the cover providing electrical insulation to at least one of the plug and the receptacle.

11. An electrical connector for making multiple electrical connections, the connector comprising:
   a plug comprising a plastic body comprising an electrically conductive layer plated directly upon the plastic body of the plug;
   a receptacle, the receptacle being mateable with the plug, the receptacle comprising a plastic body comprising an electrically conductive layer plated directly upon the plastic body of the receptacle; and
   a cover substantially surrounding at least one of the plug and the receptacle and providing electrical insulation to at least one of the plug and the receptacle, such that when a plurality of conductive cables are positioned adjacent the plug, said cables are terminated to the electrical conductive layer of the plug and the electrically conductive layer of the receptacle.

12. The electrical connector of claim 11, wherein the plug and the receptacle comprise a substantially cylindrical shape.

13. The electrical connector of claim 11, wherein the electrically conductive layer is plated on the body with a molded interconnect device technology.

\* \* \* \* \*